United States Patent [19]
Andrieu et al.

[11] Patent Number: 6,069,165
[45] Date of Patent: May 30, 2000

[54] PHARMACEUTICAL COMPOSITIONS CONTAINING AMISULPRIDE AND THEIR THERAPEUTIC APPLICATIONS

[75] Inventors: Véronique Andrieu, Nimes; Alain Cuine, Saint Fargeau-Ponthierry; Jean Montel, Chatou, all of France

[73] Assignee: Synthelabo, Le Plessis Robinson, France

[21] Appl. No.: 09/254,686

[22] PCT Filed: Sep. 17, 1997

[86] PCT No.: PCT/FR97/01633

§ 371 Date: Mar. 16, 1999

§ 102(e) Date: Mar. 16, 1999

[87] PCT Pub. No.: WO98/11881

PCT Pub. Date: Mar. 26, 1998

[30] Foreign Application Priority Data

Sep. 18, 1996 [FR] France ................................ 96 11391

[51] Int. Cl.⁷ .............................................. A61K 31/3140
[52] U.S. Cl. ............................................................ 514/428
[58] Field of Search ............................................. 514/428

[56] References Cited

U.S. PATENT DOCUMENTS

| | | | |
|---|---|---|---|
| 4,401,822 | 8/1983 | Thominet et al. | 548/567 |
| 5,446,070 | 8/1995 | Mantelle | 514/772.6 |
| 5,980,882 | 11/1999 | Eichman | 424/78.12 |

FOREIGN PATENT DOCUMENTS 2 415 099   8/1979   France .

OTHER PUBLICATIONS

J. Reynolds et al., "Martindale The Extra Pharmacopoeia", Royal Pharmaceutical Society, XP002032111, 1996.

*Primary Examiner*—James H. Reamer
*Attorney, Agent, or Firm*—Finnegan, Henderson, Farabow, Garrett & Dunner, L.L.P.

[57] ABSTRACT

A pharmaceutical composition, comprising a lipophilic phase and, as active principle, at least one compound selected from

- an optically active isomer or a racemate of amisulpride;
- an optically active isomer or a racemate of a pharmaceutically acceptable acid addition salt of amisulpride;
- an optically active isomer or a racemate of a quaternary ammonium salt of amisulpride; and
- an optically active isomer or a racemate of an oxide of amisulpride.

12 Claims, 2 Drawing Sheets

PHARMACEUTICAL COMPOSITIONS CONTAINING AMISULPRIDE AND THEIR THERAPEUTIC APPLICATIONS

This application is a 371 of PCT/FR97/01633 filed Sep. 17, 1997.

The subject of the present invention is new pharmaceutical compositions, typically suitable for oral administration, comprising 4-amino-N-[(1-ethylpyrrolidin-2-yl)methyl]-5-(ethylsulphonyl)-2-methoxybenzamide (or amisulpride), its isomers and some of their derivatives, these compositions exhibiting an improved bioavailability.

Amisulpride, its isomers and some of their derivatives are described in French Patent 78 01632, the teaching of which is integrally incorporated in the present description. Amisulpride is a neuroleptic used in the treatment of psychoses, more particularly in the treatment of paranoid and productive schizophrenias or acute delirious psychoses and in the treatment of schizophrenia deficiency states, residual psychotic changes and inhibitory states with slowing. Amisulpride is also useful in the treatment of dysthymia.

Amisulpride can be administered by the oral route, generally in the form of tablets each containing a dose of 50 or 200 mg (see Vidal, Solian heading, page 1463 and 1464, published by Vidal, 1996). The daily doses of amisulpride thus administered are often very high and can exceed 1 g/day. In this case, the patients treated with amisulpride must absorb several of these tablets daily. Some of these patients, because of their condition itself, can encounter difficulties in regularly absorbing, without forgetting, a high number of tablets and in thus correctly following their treatment.

The Applicant Company has thus sought to develop a new amisulpride form, intended mainly for administration by oral route, which only requires a limited daily number of intakes (or number of doses/day), indeed a single daily intake.

Tablets comprising a higher dose of amisulpride, for example doses greater than 600 mg, were first of all envisaged. However, such tablets often proved to be too large to be easily swallowed by the patients.

Moreover, and without being committed to the theory, the Applicant Company was able to observe that the limited bioavailability (of the order of 35 to 45%) of amisulpride administered by the oral route could be attributed to partial and uneven passage of this compound at the gastrointestinal level and that consequently, its passage at the cerebral level could sometimes be insufficient.

It was then envisaged to prolong and/or to intensify the gastrointestinal absorption of amisulpride in order to improve the bioavailability thereof, for the purpose, in particular, of decreasing the number of daily intakes of amisulpride while maintaining, indeed while improving, the therapeutic effectiveness of this compound.

The main subject of the invention is consequently a new amisulpride form exhibiting an improved bioavailability, in particular when administered by the oral route.

More specifically, the invention comprises a new pharmaceutical composition, typically suitable for oral administration, comprising a lipophilic phase and, as active principle, at least one compound selected from an optically active isomer or a racemate of amisulpride and an optically active isomer or a racemate of a pharmacologically acceptable acid, a quaternary ammonium salt or an oxide of amisulpride.

Figure 1:
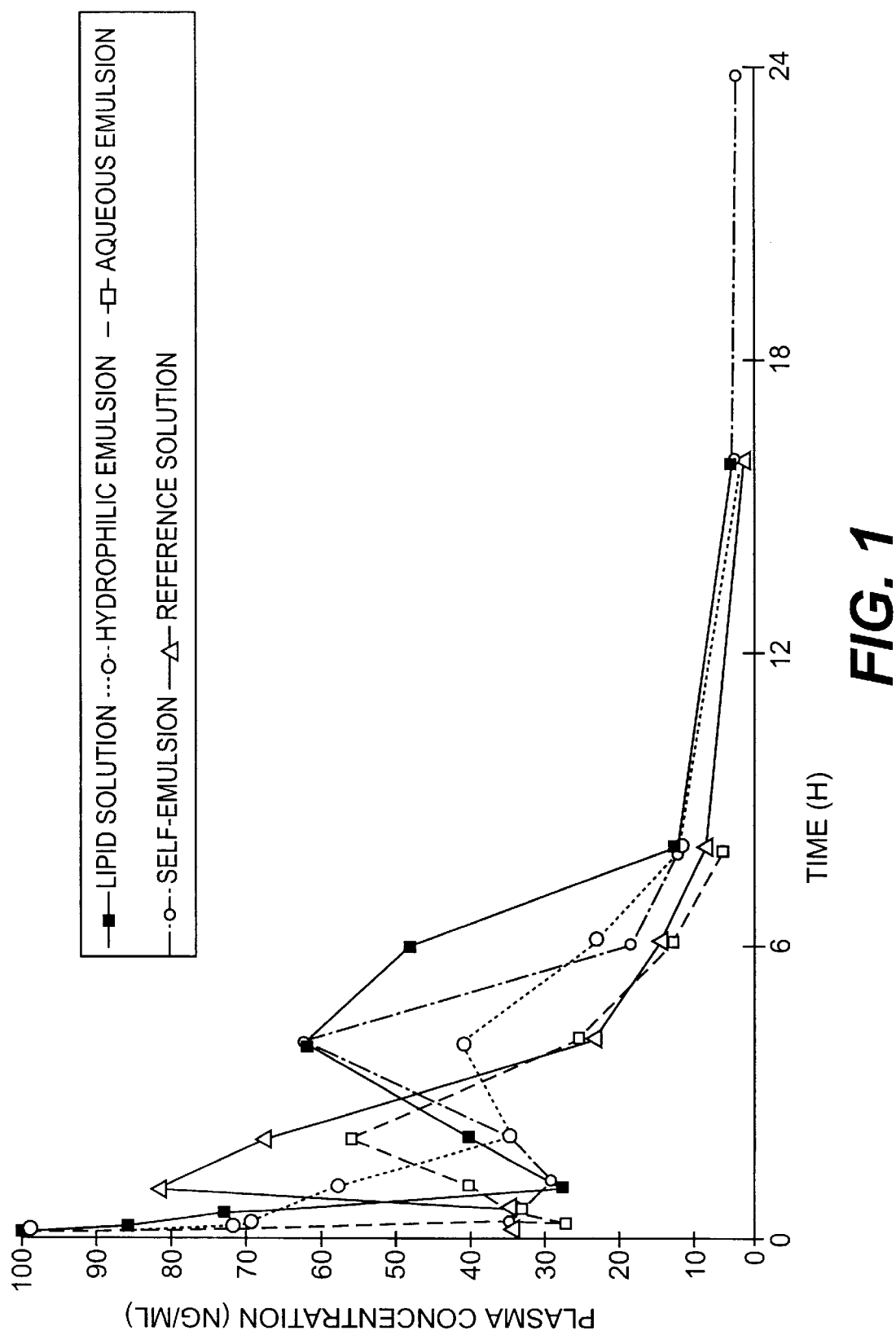
FIG. 1 represents the plasma concentrations of amisulpride, measured in the rat after absorption of various formulations comprising the same amisulpride dose.

Generally, the said active principle is dissolved, partially or completely, in the lipophilic phase.

A composition according to the invention is very particularly suitable for the administration of amisulpride per se, that is to say 4-amino-N-[(1-ethylpyrrolidin-2-yl)methyl]-5-(ethylsulphonyl)-2-methoxybenzamide, its laevorotatory ((S)-(−)-amisulpride) and dextrorotatary ((R)-(+)-amisulpride) isomers, mixtures of these isomers. It is also particularly suitable for the administration of tartrates of amisulpride per se and of its isomers, and more particularly tartrates of the said isomers and mixtures of these tartrates. A preferred tartrate consists of the compound described in Example IV of Patent FR 78 01632, that is to say the (D)-tartrate of (S)-(−)-amisulpride, in other words (S)-(−)-4-amino-N-[(1-ethylpyrrolidin-2-yl)methyl]-5-(ethylsulphonyl)-2-methoxybenzamide [S-(R*,R*)]-2,3-dihydroxybutanedioate.

A composition according to the invention can also be suitable for the administration of other derivatives of amisulpride as mentioned above. These derivatives and their process of preparation are described in more detail in French Patent 78 01632, which has already been mentioned. Mention may more particularly be made, as acids which are suitable for forming salts of amisulpride per se and of its isomers, of hydrochloric, hydrobromic, sulphuric, phosphoric, oxalic, acetic, tartaric, citric and methanesulphonic acids.

For reasons of simplicity, and unless otherwise indicated, "amisulpride" will be understood as meaning, in the description below, both amisulpride per se as well as its isomers and its derivatives mentioned above.

The compositions according to the invention make it possible to increase in particular the bioavailability of amisulpride with respect to conventional oral formulations.

Because of this improved bioavailability, it is then possible to solve the problem consisting in making available amisulpride forms which only require a limited number of daily intakes. This is because the improvement in the bioavailability obtained makes it possible to significantly reduce the amisulpride doses administered.

In the context of the present invention, the term "bioavailability" is understood to mean the fraction of the active principle which is absorbed from its pharmaceutical form and which arrives at the site of action.

A pharmaceutical composition according to the invention can comprise from 25 to 300 mg, more preferably from 100 to 250 mg, of amisulpride/unit dose. Such a content allows the administration of only one to three unit doses per day, preferably one to two unit doses per day.

The amisulpride concentration in a pharmaceutical composition of the invention can be between 1 mg/ml and 350 mg/ml, preferably between 10 mg/ml and 310 mg/ml.

The lipophilic phase can be solid or, preferably, liquid at room temperature.

The lipophilic phase can comprise (i) one or more fatty acids, (ii) one or more monoglycerides or one or more acetylated or polyethoxylated derivatives of monoglycerides, (iii) one or more diglycerides or one of more acetylated or polyethoxylated derivatives of diglycerides, (iv) one or more oils, such as mineral, animal, vegetable, transesterified and/or polyethoxylated vegetable oils, or synthetic oils, or (v) a mixture comprising two or more of the compounds mentioned in two or more of parts (i), (ii), (iii) and (iv), in particular a mixture comprising a fatty acid and an oil.

Mention may be made, by way of fatty acids, of those comprising from 12 to 22 carbon atoms, in particular oleic, arachidonic, linolenic, linoleic or ricinoleic acids.

Mention may particularly be made, by way of monoglycerides, diglycerides or acetylated or polyethoxylated derivatives of these compounds, of those comprising, respectively, one or two fatty chains comprising from 12 to 24 carbon atoms and more particularly those sold by the companies Abitec and Eastman under the trade marks Capmul® and Myvacet®, in particular glycerol monocaprylate, glycerol monostearate, monoacetylated monoglycerides and diacetylated monoglycerides.

Mention may be made, by way of mineral oils which are suitable in the context of the invention, of liquid paraffins and liquid petrolium.

Mention may be made, by way of vegetable oils, of olive, groundnut, soybean, rapeseed, palm, sesame, grape seed, maize, walnut or sunflower oils. Mention may be made, by way of transesterified and/or polyethoxylated vegetable oils, of polyethoxylated olive, polyethoxylated sunflower, polyethoxylated palm or polyethoxylated castor oils, in particular those sold under the trade mark Labrafil® by the company Gattefossé.

Mention may be made, by way of animal oils, of liver oils, in particular cod or halibut liver oils. Mention may be made, by way of synthetic oils, of silicone oils.

Oleic acid constitutes a particularly preferred lipophilic phase.

The lipophilic phase can be provided in the from either of an emulsion or of a self-emulsifiable mixture.

Such an emulsion, in addition to the lipophilic phase, comprises a hydrophilic phase and, generally, at least one surface-active agent. The emulsion can be of the water-in-oil (W/O) or, preferably, oil-in-water (O/W) type. Emulsion can be of the submicronic emulsion type. Such an emulsion exhibits a non-continuous phase in the form of particles with a mean diameter of less than 1 µm, generally of between 0.3 and 0.7 µm. The emulsion can also be of the microemulsion type, for which the non-continuous phase generally exists in the form of particles with a mean diameter of between 0.05 and 0.250 µm.

The hydrophilic phase can be composed of one or more compounds chosen from alcohols, such as glycerol, propylene glycol, polyethylene glycols with a molecular weight of between 100 and 3000, or water. The latter is preferred in the context of the present invention.

The dispersed phase of an emulsion according to the invention can represent from 5 to 30% by weight, generally from 10 to 20% by weight, of the total weight of the emulsion.

The surface-active agent is chosen as a function of the nature of the emulsion. The person skilled in the art knows, in particular as a function of its HLB (Hydrophile-Lipophile Balance), which surface-active agent to choose in order to obtain a W/O or O/W emulsion or a microemulsion.

Mention may be made, by way of surface-active agent which can be suitable in the context of the present invention, of sorbitan esters and polyoxyethylenated esters of sorbitan, such as those sold under the trade marks Tween® and Span®, lecithins of animal or vegetable origin, polyoxyethylenated castor oils, such as those sold under the trade mark Cremophor®, esters of sucrose and of fatty acids (or sucroesters), esters of fatty alcohols and of polyethylene glycol, esters of fatty acids and of polyethylene glycol, or bile acids, it being possible for these surface-active agents to be used alone or as a mixture.

An emulsion according to the invention can comprise from 0.01 to 5% by weight of surface-active agents with respect to the dispersed phase.

Within the meaning of the present invention, the term "self-emulsifiable mixture" is understood to mean a mixture composed of a lipophilic phase, comprising at least one oil and/or at least one fatty acid, such as those described above, with at least one surface-active agent, it being possible for this mixture to form an emulsion by simple mechanical stirring with an aqueous phase. A self-emulsifiable mixture according to the invention can, after administration by the oral route, form emulsions with the hydrophilic phases of the body.

The constituent surface-active agents of such a self-emulsifiable mixture can be chosen from sorbitan esters and polyoxyethylenated esters of sorbitan, such as those sold under the trade marks Tween® and Span®, in particular polysorbate 80.

The content of surface-active agents in the self-emulsifiable mixture can be between 0.5 and 10% by weight with respect to the lipophilic phase.

The pharmaceutical composition according to the invention is advantageously provided in the form of a lipid solution. The latter essentially comprises a lipophilic phase, generally comprising at least one fatty acid and/or at least one oil, such as those mentioned above, the amisulpride being dissolved in this lipophilic phase. Such a lipid solution is typically substantially free of hydrophilic phase and of surface-active agent. The lipophilic phase of the lipid solution is preferably composed of a fatty acid, more preferably oleic acid.

A pharmaceutical composition according to the invention can in addition comprise pharmaceutically acceptable excipients, such as diluents, preserving agents, osmotic agents, antioxidants, thickening agents, stabilizing agents, viscosity-reducing agents such as ethanol, gelling agents and pH buffers.

The pharmaceutical compositions of the invention can be prepared by methods known to a person skilled in the art.

Thus, a lipid solution according to the invention can be prepared by dissolving amisulpride with stirring in the lipophilic phase. If appropriate, other excipients, such as those mentioned above, can then be added.

For the purpose of the preparation of an emulsion, the lipophilic phase containing amisulpride can be introduced, with stirring, into the hydrophilic phase to which the surface-active agent(s) and, if appropriate, hydrophilic excipients have been added beforehand. Stirring can be carried out by means of a device of the Ultra-Turrax® type.

For the purpose of the preparation of a submicronic emulsion, the emulsion thus obtained can be refined by means of a very high pressure dye, for example of the APV-Gaulin® type.

A self-emulsifiable mixture according to the invention can be prepared conventionally by introducing, with stirring, the required surface-active agent(s) into a lipophilic phase containing amisulpride, this lipophilic phase itself being prepared as indicated above.

A composition according to the invention can be presented in the divided or undivided liquid form, optionally accompanied by a measuring device such as a spoon, in the gelled form, in the form of soft capsules or of globules, or, preferably, in the form of hard gelatin capsules. These hard gelatin capsules can be composed of gelatin or of starch and are usually sealed conventionally.

The pharmaceutical compositions according to the invention are mainly and preferably intended for administration by the oral route. They can, however, be administered by other routes, for example by the rectal route.

According to another aspect, the invention relates to the use of amisulpride for preparing the pharmaceutical compositions described above, for the treatment of dysthymia, the treatment of psychoses, more particularly for the treatment of paranoid and productive schizophrenias or acute delirious psychoses, and for the treatment of schizophrenia deficiency states, residual psychotic changes and inhibitory states with slowing. The said pharmaceutical compositions can also be employed in the therapeutic treatment of delirious fits, hebephreno-catatonia or migraines, with or without photophobia or nausea. Moreover, because of the inhibiting effect of amisulpride, they can be used in the treatment of autism. They also prove to be useful in withdrawal related to the consumption of alcohol and/or of drugs and/or of tobacco; more particularly, they make it possible to decrease the risks of relapse during the post-withdrawal deficiency period.

According to yet another aspect, the invention relates to new pharmaceutical compositions comprising amisulpride and at least one pharmaceutically acceptable excipient, the said compositions allowing the prolongation and/or intensification of the gastrointestinal absorption of amisulpride, so that the bioavailability of the amisulpride is greater than 50%, more generally of between 60 and 75%. These pharmaceutical compositions are typically intended for oral administration. The compositions comprising a lipophilic phase and amisulpride which are described above make it possible to confer such a bioavailability.

The following Examples illustrate the present invention.

EXAMPLE 1

Self-emulsifiable Mixture Suitable for the Rat

A self-emulsifiable mixture according to the invention is prepared by introducing 100 mg of amisulpride per se and 4 mg of polysorbate 80 in oleic acid (q.s. for 100 ml). The mixture is then slowly stirred until dissolution is complete.

EXAMPLE 2

O/W Submicronic Emulsion Suitable for the Rat

An O/W submicronic emulsion according to the invention is prepared in the following way:

A hydrophilic phase is prepared by mixing 3.3 g of soybean lecithin, 5.6 g of glycerol, 2 g of solidified polyoxyethylenated castor oil (Cremophor® RH 40) and 0.1 g of sodium hydrogensulphite. This mixture is dissolved or dispersed in 82 g of water and heating is carried out at 70–80° C.

Moreover, a lipophilic phase is prepared by heating a solution of 6.25 g of amisulpride per se and of 1.3 g of a sucroester of HLB=15 in 22.25 g of oleic acid at 70–80° C.

The lipophilic phase is added to the hydrophilic phase and stirring is carried out with an Ultra-Turrax® stirrer, at 5000 revolutions/min, for ten minutes.

A coarse emulsion is thus obtained which is refined by means of a very high pressure homogenizer of the APV-Gaulin® type, in order to obtain a liquid emulsion in which the mean diameter of the lipophilic particles is less than 1 $\mu$m.

EXAMPLE 3

O/W Hydrophilic Emulsion Suitable for the Rat

An O/W hydrophilic emulsion according to the invention is prepared in the following way:

A 2.25 mg/ml solution of polysorbate 80 in doubly-distilled glycerol is mixed with a lipid solution of amisulpride per se in oleic acid. This mixture is then stirred with an Ultra-Turrax® stirrer, at 5000 revolutions/min, for ten minutes.

An emulsion is thus obtained comprising:

|  |  | % mass/vol. |
|---|---|---|
| amisulpride per se |  | 1 |
| oleic acid |  | 9.1 |
| polysorbate 80 |  | 2.25 |
| glycerol | q.s. for | 100 |

EXAMPLE 4

O/W Aqueous Emulsion Suitable for the Rat

An O/W aqueous emulsion according to the invention is prepared in the following way:

A hydrophilic phase is prepared by mixing soybean lecithin, solidified polyoxyethylenated castor oil (Cremophor RH 40®) and sodium hydrogensulphite. This mixture is dissolved or dispersed in water (q.s. for 100 ml) and the mixture is heated at 70–80° C. Moreover, a lipophilic phase composed of a solution of amisulpride per se in oleic acid is prepared. The lipophilic phase is added to the hydrophilic phase and stirring is carried out with an Ultra-Turrax® stirrer, at 5000 revolutions/min, for ten minutes. An emulsion is thus obtained comprising:

|  |  | % mass/vol. |
|---|---|---|
| amisulpride per se |  | 1 |
| oleic acid |  | 9.1 |
| soybean lecithin |  | 1.34 |
| polyoxyethylenated castor oil |  | 0.8 |
| sodium hydrogensulphite |  | 0.04 |
| purified water | q.s. for | 100 |

EXAMPLE 5

Lipid Solution Suitable for the Rat

Amisulpride per se was introduced, with slow stirring, into oleic acid, so as to obtain a 10 mg/ml lipid solution of amisulpride per se in accordance with the invention.

EXAMPLE 6

Lipid Solution for Human Use

Amisulpride per se was introduced, with slow stirring, into oleic acid, so as to obtain a 25 mg/ml lipid solution of amisulpride.

This solution was divided into size 1 hard gelatin capsules in the proportion of 0.4 g per hard gelatin capsule. Each hard gelatin capsule contained 100 mg of amisulpride per se.

EXAMPLE 7

Example 6 was repeated, the amisulpride per se being replaced by (S)-(−)-amisulpride (D)-tartrate, that is to say the compound of Example IV of Patent FR 78 01632. Hard gelatin capsules containing 100 mg of active principle were thus obtained.

EXAMPLE 8

Pharmaceutical compositions in accordance with the invention were tested on the rat, according to the following protocol:

The rats were Sprague Dawley OFA male rats weighing from 200 to 220 g and 7 weeks old.

After administration of the pharmaceutical composition in accordance with or not in accordance with the invention ($T_0$), the animals were returned to their cage. They were deprived of food for at most four hours after treatment. Samples were removed from the inferior vena cava at times 0, 0.08, 0.25, 1, 2, 4, 6, 8, 16 and 24 hours. The tubes containing the withdrawn blood were centrifuged and the recovered plasma was stored in a freezer.

The concentration of amisulpride per se in the plasma was measured by HPLC with detection by fluorimetry.

Pharmaceutical compositions according to the invention, each comprising 10 mg/ml of amisulpride per se, were tested.

The compositions tested were those of Examples 1, 3, 4 and 5.

These compositions were compared with a reference solution, not in accordance with the invention, composed of a 0.9% aqueous sodium chloride solution comprising 10 mg/ml of amisulpride per se, the pH of which was adjusted to 3.5–6.5 by means of 1M hydrochloric acid.

All the compositions tested were administered by the oral route.

The results obtained are reported in FIG. 1. The plasma concentrations of amisulpride per se are expressed in ng/ml.

The $T_{max}$ and $C_{max}$ values and the areas under the curve (AUC) obtained for each composition tested are combined in Table I below.

TABLE I

| Pharmaceutical form | $T_{max}$ (hours) | $C_{max}$ (ng/ml) | AUC (ng/ml/h) (T1 – T2) |
| --- | --- | --- | --- |
| Reference solution | 1 | 82 | 287 (0.08 – 16) |
| Lipid solution | 0.08 | 108 | 410 (0.08 – 16) |
| Aqueous emulsion | 0.08 | 110 | 213 (0.08 – 8) |
| Hydrophilic emulsion | 0.08 | 107 | 310 (0.08 – 16 |
| Self-emulsifiable mixture | 4 | 63 | 324 (0.08 – 24) |

These results show the decrease in The $T_{max}$ and/or the increase in the AUC when amisulpride per se is administered in accordance with the invention; this demonstrates an intensification in the absorption of amisulpride per se and thus an improvement in its bioavailability.

EXAMPLE 9

Lipid solutions comprising increasing concentrations of amisulpride per se were tested according to the protocol described in Example 8.

The lipid solutions were prepared by stirring the required dose of amisulpride per se in 10 ml of oleic acid until dissolved.

The lipid solutions were compared with a reference solution composed of an aqueous sodium chloride solution comprising 50 mg/ml of amisulpride per se, the pH of which was adjusted to 3.5–6.5 by means of 1M hydrochloric acid.

Figure 2:
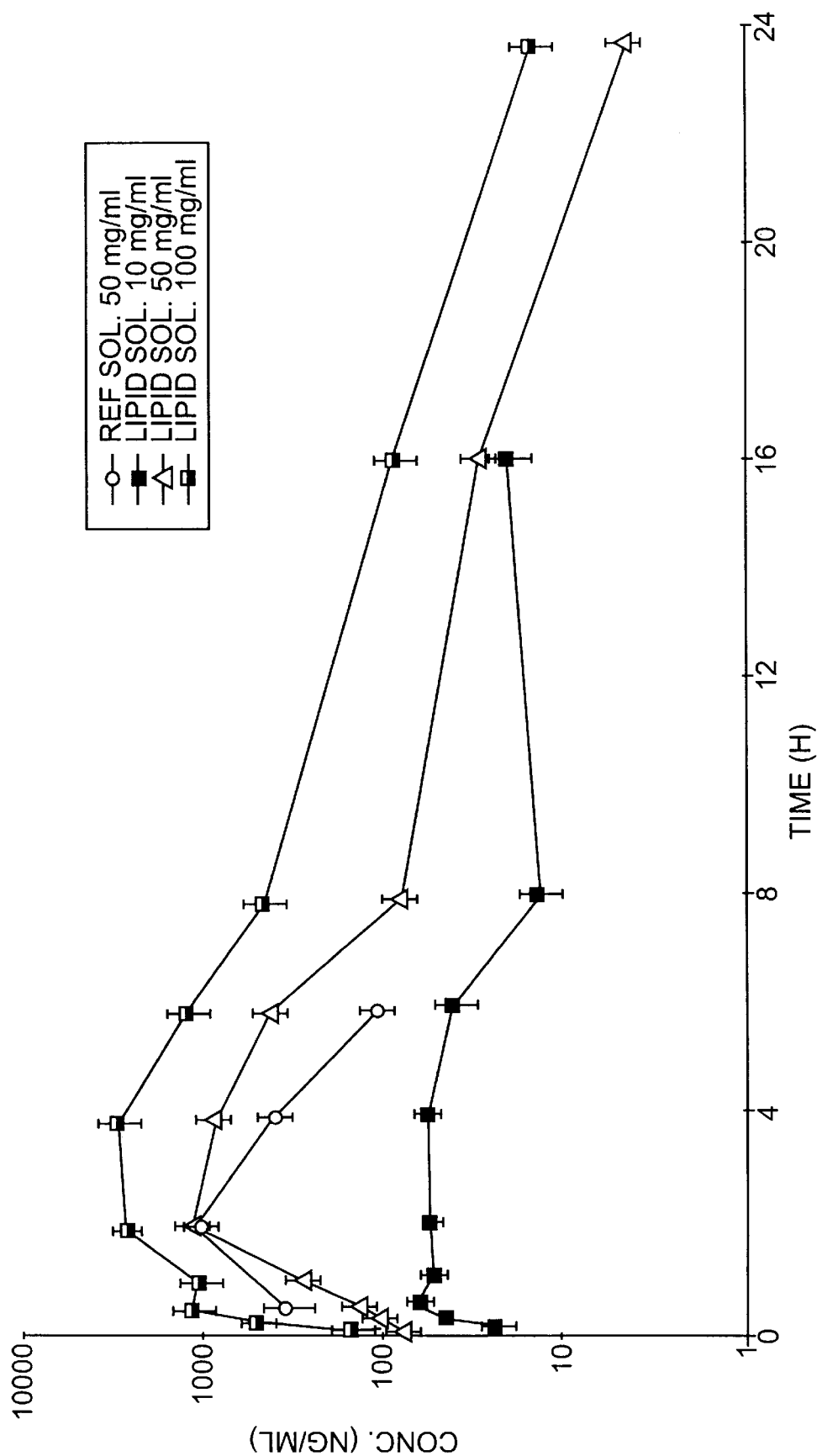
FIG. 2 represents the plasma concentrations of amisulpride, measured in the rat after absorption of formulations comprising variable amisulpride doses.

The results obtained are reported in FIG. 2. The plasma concentrations of amisulpride per se are expressed in ng/ml.

The $T_{max}$ and $C_{max}$ values and the areas under curve (AUC) obtained for each composition tested are combined in Table II below.

TABLE II

| Pharmaceutical form | $T_{max}$ (hours) | $C_{max}$ (ng/ml) | AUC (ng/ml/h) (T1 – T2) |
| --- | --- | --- | --- |
| Reference solution 50 mg/ml | 2 | 1075 | 3138 (0.08 – 6) |
| Lipid solution 10 mg/ml | 0.5 | 72 | 511 (0.08 – 16) |
| Lipid solution 50 mg/ml | 2 | 1142 | 4981 (0.08 – 6) |
| Lipid solution 100 mg/ml | 4 | 2871 | 15,848 (0.08 – 16 |

These results show the intensification and the prolongation of the absorption and thus the increase in the bioavailability of amisulpride per se administered in the form of a lipid solution in accordance with the invention.

What is claimed is:

1. An oral pharmaceutical composition which comprises a lipophilic phase and at least one active principle composed of amisulpride, one of its laevorotatory and dextrorotatory isomers or a derivative of amisulpride or of one of its laevorotatory and dextrorotatory isomers, said derivative being chosen from an addition salt with a pharmacologically acceptable acid, a quaternary ammonium salt or an oxide of amisulpride or of one of its laevorotatory and dextrorotatory isomers.

2. An oral composition according to claim 1, wherein the lipophilic phase comprises (i) one or more fatty acids, (ii) one or more monoglycerides or acetylated or polyethoxylated derivatives of monoglycerides, (iii) one or more diglycerides or acetylated or polyethoxylated derivatives of diglycerides, (iv) one or more oils, such as mineral, animal, vegetable, transesterified and/or polyethoxylated vegetable, or synthetic oils, or (v) a mixture comprising two or more of the compounds mentioned in parts (i), (ii), (iii) and (iv).

3. An oral composition according to claim 1 wherein the lipophilic phase comprises oleic acid.

4. An oral composition according to claim 1, wherein the composition is in the form of a lipid solution, of an emulsion or of a self-emulsifiable mixture.

5. An oral composition according to claim 1, wherein the composition is provided in the form of a microemulsion.

6. An oral composition according to claim 1, wherein said active principle comprises amisulpride, the levorotatory isomers of amisulpride, the dextrorotatory isomer of amisulpride or one of their tartrates.

7. An oral composition according to claim 6, wherein said active principle comprises the laevorotatory isomers of amisulpride or one of its tartrates, in particular (S)-(–)-amisulpride (D)-tartrate.

8. An oral composition according to claim 1, further comprising at least one surface-active agent when the composition is in the form of an emulsion or of a self-emulsifiable mixture.

9. An oral composition according to claim 1, comprising from 50 to 300 mg of the said active principle per dose.

10. An oral composition according to claim 9, comprising from 100 to 250 mg of the said active principle per dose.

11. An oral composition according to claim 1, in the form of hard gelatin capsules.

12. A method for the treatment of dysthymia, psychoses, paranoid and productive schizophrenias, acute delirious psychoses, schizophrenia deficiency states, or residual psychotic changes and inhibitory states with slowing, comprising administering an effective amount of the pharmaceutical composition of claim 1, to a patient in need thereof.

* * * * *